US00PP19500P2

(12) United States Plant Patent
Kawashima et al.

(10) Patent No.: US PP19,500 P2
(45) Date of Patent: Nov. 25, 2008

(54) **NEW GUINEA *IMPATIENS* PLANT NAMED 'SAKIMP005'**

(50) Latin Name: *Impatiens×hybrida*
Varietal Denomination: SAKIMP005

(75) Inventors: Moriya Kawashima, Nagano (JP); Yoneo Kobayashi, Shizuoka (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 11/895,964

(22) Filed: Aug. 28, 2007

(51) Int. Cl.
*A01H 5/00* (2006.01)

(52) U.S. Cl. ..... Plt./318.3

(58) Field of Classification Search ..... Plt./318.3, Plt./318.4, 318.7
See application file for complete search history.

*Primary Examiner*—Kent L. Bell
*Assistant Examiner*—June Hwu
(74) *Attorney, Agent, or Firm*—Jondle & Associates, P.C.

(57) ABSTRACT

A New Guinea *Impatiens* cultivar particularly distinguished by having large, pinkish-red flowers, vigorous rooting, spreading growth habit and variegated leaves is disclosed.

1 Drawing Sheet

Genus and species: *Impatiens×hybrida.*
Variety denomination: 'SAKIMP005'.

BACKGROUND OF THE NEW PLANT

The present invention comprises a new and distinct cultivar of New Guinea *Impatiens,* botanically known as *Impatiens×hybrida,* and hereinafter referred to by the cultivar name 'SAKIMP005'. 'SAKIMP005' originated from an interspecific hybridization between 'NG-02WM1', an unpatented proprietary deep-orange flowered *Impatiens* plant and 'NG-01H-15B', an unpatented proprietary magenta flowered *Impatiens* plant, in Misato, Japan.

In April 2002, the female parent line 'NG-02WM1' and male parent line 'NG-01H-15B' were crossed and a population of $F_1$ plants was created. The $F_1$ plants were evaluated in Misato, Japan in an open field trial. The criteria for plant selection included spreading growth habit, vigorous rooting, pinkish-red flower color and variegated leaves. At the completion of the trial, one single-plant selection was made based on the above criteria and vegetatively propagated. From May to August 2004, the selection was evaluated in an open field in Misato, Japan. The selection was also evaluated in an open field trial during the summer of 2004 in Athens, Ga., USA. Shoot-tip cuttings of the variety were then shipped in Salinas, Calif., where the plants were regenerated and reevaluated for stability of traits. The selection subsequently was named 'SAKIMP005' and found to have its unique characteristics reproduce true to type in successive generations of asexual propagation. The instant plant was asexual reproduced by vegetative cutting in Salinas, Calif.

Plant Breeder's Rights for this cultivar were applied for in Canada on Mar. 28, 2007.

SUMMARY OF THE INVENTION

The following are the most outstanding and distinguishing characteristics of this new cultivar when grown under normal horticultural practices in Salinas, Calif.

1. Pinkish-red flower color;
2. Spreading growth habit;

3. Vigorous rooting; and
4. Variegated leaves.

DESCRIPTION OF PHOTOGRAPHS

This new *Impatiens* plant is illustrated by the accompanying photographs which show overall plant habit including blooms, buds, and foliage of the plant; the colors shown are as true as can be reasonably obtained by conventional photographic procedures.

Figure 1:
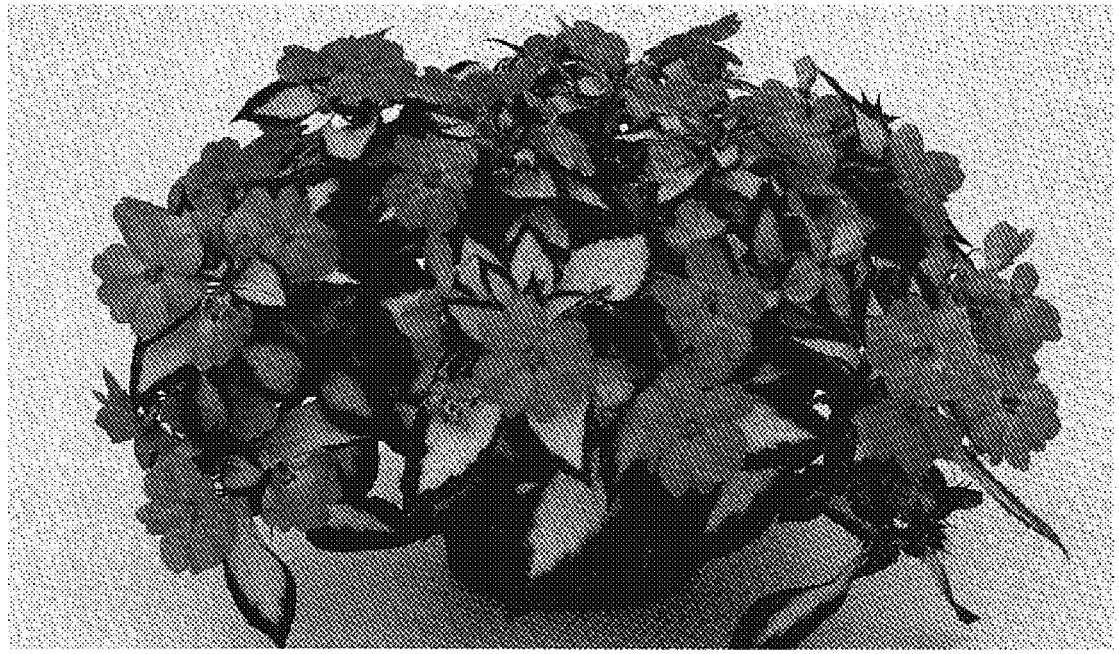

FIG. 1 The photograph shows overall plant habit including blooms, buds and foliage.

Figure 2:
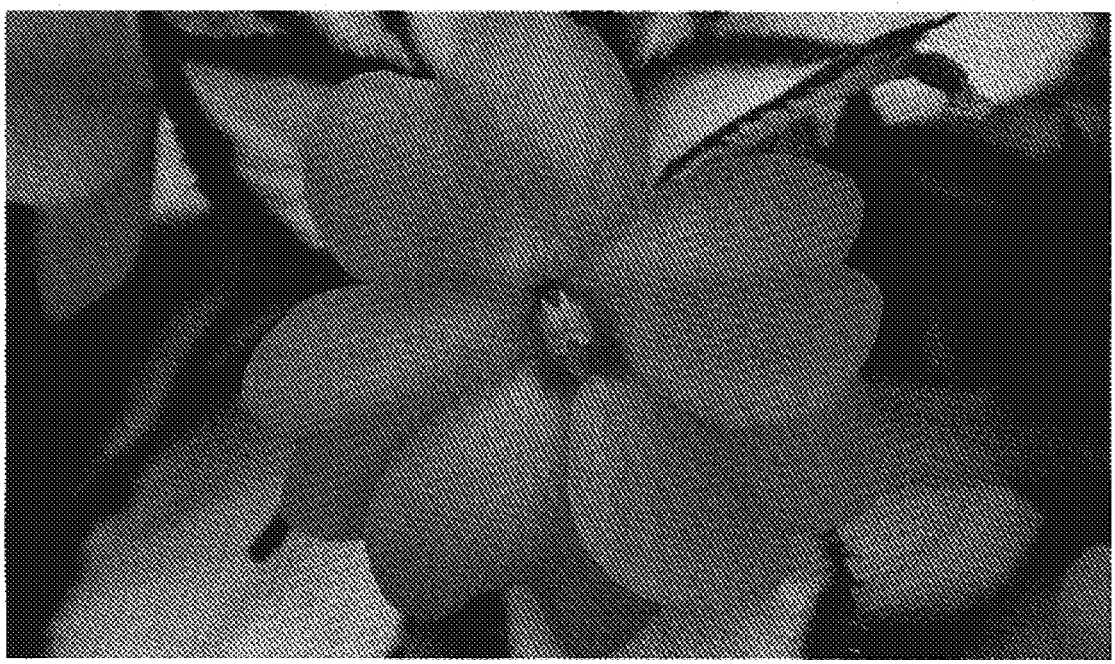

FIG. 2 The photograph shows the mature inflorescence.

DETAILED DESCRIPTION OF THE NEW CULTIVAR

The following detailed descriptions set forth the distinctive characteristics of 'SAKIMP005'. The data which define these characteristics were collected from asexual reproductions carried out in Salinas, Calif. The plant history was taken on plants grown for about four months from propagation by terminal cuttings under greenhouse conditions. Color references are primarily to the R.H.S. Colour Chart of The Royal Horticultural Society of London (R.H.S.), $4^{th}$ edition (2001). Anatomic labels are from The Cambridge Illustrated Glossy of Botanical Terms, by M. Hickey and C. King, Cambridge University Press.

DETAILED BOTANICAL DESCRIPTION

Classification:
*Family.*—Balsaminaceae.
*Botanical.*—*Impatiens×hybrida.*
*Common name.*—*Impatiens.*

Parentage:
*Female parent.*—'NG-02WM1', an unpatented proprietary deep-orange flowered *Impatiens* plant.
*Male parent.*—'NG-01H-15B', an unpatented proprietary magenta flowered *Impatiens* plant.

Growth:

*Time to produce a rooted cutting.*—The terminal 1.0 to 1.5 inches of an actively growing stem was excised. The vegetative cuttings were propagated in five to six weeks. The base of the cuttings were dipped for 1 to 2 seconds in a 1:9 solution of Dip 'N Grow (1 solution: 9 water) root inducing solution immediately prior to sticking into the cell trays. Cuttings were stuck into plastic cell trays having 98 cells, and containing a moistened peat moss-based growing medium. The cuttings were misted with water from overhead for 10 seconds every 30 minutes until sufficient roots were formed.

*Environmental conditions for plant growth.*—Rooted cuttings were transplanted and grown in 6-inch plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Plants were fertilized every 2–3 days, 2 times in consecutive applications and then given one clear water application. Pots were top-dressed with a dry, slow release fertilizer containing 14% nitrogen, 14% phosphorus and 14% potassium. The typical average air temperature was 24° C.

*Time to bloom from propagation.*—6 to 8 weeks.

Plant description:

*Habit.*—Spreading, trailing.

*Height.*—16.0 cm to 18.0 cm from soil line to top of foliage.

*Spread.*—52.0 cm to 54.0 cm.

*Time to produce a finished flowering plant.*—6 to 8 weeks.

*Time to produce a rooted cutting.*—4 weeks.

*Flowering requirements.*—Will flower so long as temperature is above 5° C.

*Temperature tolerance.*—Plants have been observed to continuously flower at a temperature range of 5° C. to 36° C.

Branches:

*Number.*—14 total with 5 main branches.

*Length.*—4.0 cm from soil line to first node; 12.0 cm to 15.0 cm total.

*Diameter (main branch).*—1.0 cm.

*Color.*—RHS 185A (Greyed-Purple).

Stems:

*Length.*—5.0 cm from first to second node.

*Diameter.*—0.5 cm to 0.7 cm.

*Internode length.*—4.0 cm to 5.0 cm.

*Color.*—RHS 185A (Greyed-purple).

*Stem description.*—Strong; circular cross-section, smooth and shiny.

*Pubescence.*—Absent.

*Anthocyanin color.*—RHS 185D (Greyed-purple).

*Peduncles.*—Length: 3.0 cm. Diameter: 0.1 cm to 0.15 cm. Color: RHS 56D (Red). Texture: Smooth, glabrous.

Leaves:

*Arrangement.*—Whorled with up to 5 leaves per node, opposite if only two leaves at one node.

*Length.*—7.0 cm to 9.0 cm.

*Width.*—3.0 cm to 4.0 cm.

*Shape.*—Lanceolate, curled.

*Margin.*—Serrate.

*Apex.*—Acuminate.

*Base.*—Shortly attenuate.

*Color.*—Upper surface: Variegated, RHS 139A (Green) around outer edge with RHS 11B (Yellow) from inside edge to center. Lower surface: RHS 191A (Greyed-green) around outer edge with RHS 11C (Yellow) from inside edge to center.

*Texture.*—Dull; waxy.

*Variegation.*—Yellow area: Length: 5.5 cm to 6.0 cm. Diameter: 0.4 cm to 0.5 cm. Green area: Diameter: 0.3 cm to 1.0 cm around outer edge.

*Fragrance.*—Absent.

*Pubescence.*—Absent.

*Venation.*—Pinnate.

*Venation color.*—Upper surface: RHS 11D (Yellow). Lower surface: RHS 11D (Yellow) to edge, the RHS 191A (Greyed-green) at rim.

*Petioles.*—Length: 0.8 cm to 1.0 cm. Diameter: 0.4 cm to 0.5 cm. Color: RHS 11D (Yellow). Texture: Smooth, glabrous.

Flower buds:

*Shape.*—Deltoid, longitudinal cross-section.

*Length.*—1.5 cm to 1.7 cm.

*Diameter.*—1.0 cm.

*Color.*—RHS 52B (Red) with RHS 141D (Green) at the edge.

*Texture.*—Glabrous.

Inflorescence:

*Inflorescence type.*—Single flower with spur.

*Number of flowers per node.*—1 to 3 in bloom at one time; about 10 flower buds.

*Number of flowers per plant.*—50 to 60.

*Lastingness of individual blooms on the plant.*—14 days.

*Fragrance.*—Absent.

Corolla:

*Shape.*—Roughly circular with 5 radial petals.

*Diameter.*—5.5 cm.

*Depth.*—0.1 cm to 0.2 cm.

*Petals:*

*Shape.*—Obcordate.

*Length.*—2.5 cm.

*Width.*—3.0 cm.

*Apex.*—Emarginate (cleaved).

*Base.*—Attenuate.

*Margin.*—Entire.

*Pubescence.*—Glabrous.

*Color.*—Upper surface: RHS 52B (Red). Lower surface: RHS 52D (red) with RHS 52C (Red) vein between petal lobes. Eye zone: RHS 53A (Red).

Spur:

*Shape.*—Tubular and curved downward.

*Color.*—RHS 52C (Red).

*Length.*—3.8 cm to 4.0 cm.

*Diameter.*—0.1 cm to 0.2 cm.

Sepals:

*Shape.*—Lanceolate.

*Number.*—Two.

*Color.*—RHS 145C (Yellow-green).

*Length.*—0.8 cm to 1.0 cm.

*Diameter.*—0.4 cm to 0.5 cm.

*Apex.*—Caudate.

*Base.*—Subcordate.

*Margin.*—Entire.

*Texture.*—Glabrous.

Reproductive organs:

*Stamens.*—Form: Fused; split into 4 lobes. Number: Many. Filament length: 0.3 cm. Filament color: RHS 52D (Red). Anther length: 0.4 cm. Anther color: RHS N155A (White). Pollen amount: Abundant. Pollen color: RHS N155A (White). Pollen description: Powdery.

*Pistil.*—Number: 5. Stigma color: RHS 143A (Green). Style color: RHS 143A (Green).

*Ovary arrangement.*—Parietal.

*Ovary surface color.*—RHS 1B (Green-yellow).

Fruit and seed set: No seed set observed.

Disease and insect resistance: No particular resistance or susceptibility has been observed.

COMPARISON WITH KNOWN CULTIVARS

'SAKIMP005' differs from the female parent, 'NG-02WM1', an unpatented *Impatiens* plant, in that 'SAKIMP005' has large, pinkish-red flowers while 'NG-02WM1' has medium, deep-orange flowers. Additionally, 'SAKIMP005' has a spreading growth habit, while 'NG-02WM1' has a mounding growth habit.

'SAKIMP005' differs from the male parent, 'NG-01H-15B', an unpatented proprietary *Impatiens* plant in that 'SAKIMP005' has large, pinkish-red flowers, while 'NG-01H-15B' has small, magenta flowers. Additionally, 'SAKIMP005' has a spreading growth habit, while 'NG-01H-15B' has a mounding growth habit.

'SAKIMP005' is similar to the commercial *Impatiens* variety 'Misato FG2' (U.S. Plant Pat. No. 17,663) (known commercially as 'SunPatiens Orange') however, there are differences as listed in the table below:

TABLE 1

Comparison of Characteristics between 'SAKIMP005' and 'Misato FG2'

| Characteristic | 'SAKIMP005' | 'Misato FG2' |
|---|---|---|
| Growth habit | Spreading | Upright |
| Petal color, Upper surface | RHS 52B (Red) | RHS N30C (Orange-red) |
| Spur color | RHS 52C (Red) | RHS 63A (Red-purple) at base fading to RHS 62D (Red-purple) at tip |

I claim:

1. A new and distinct cultivar of New Guinea *Impatiens* plant as shown and described herein.

* * * * *